United States Patent [19]

Agrawal et al.

[11] Patent Number: 5,403,709

[45] Date of Patent: Apr. 4, 1995

[54] METHOD FOR SEQUENCING SYNTHETIC OLIGONUCLEOTIDES CONTAINING NON-PHOSPHODIESTER INTERNUCLEOTIDE LINKAGES

[75] Inventors: Sudhir Agrawal; Jin-Yan Tang, both of Shrewsbury, Mass.

[73] Assignee: Hybridon, Inc., Worcester, Mass.

[21] Appl. No.: 958,133

[22] Filed: Oct. 6, 1992

[51] Int. Cl.$^6$ .................. C12Q 1/68; C12P 19/34; C01N 33/48
[52] U.S. Cl. .................. 435/6; 435/91.1; 436/94
[58] Field of Search ............ 435/6, 91, 91.1; 436/94

[56] References Cited

U.S. PATENT DOCUMENTS 4,797,355  1/1989  Stabinsky .................. 435/6

OTHER PUBLICATIONS

Agrawal et al., *J. Chromatog.* 509, 396–399 (1990).

*Primary Examiner*—Margaret Parr
*Assistant Examiner*—Kenneth R. Horlick
*Attorney, Agent, or Firm*—Allegretti & Witcoff, Ltd.

[57] ABSTRACT

The invention relates to synthetic oligonucleotides and more particularly to the determination of nucleotide sequences of synthetic oligonucleotides having non-phosphodiester internucleotide linkages. The invention provides a method for sequencing such modified synthetic oligonucleotides.

6 Claims, 3 Drawing Sheets

5'-CTCTGCACCCATCTCTCTCCTTCT
(Sample Oigonucleotide)

(Molecular Tack Oligonucleotide)
*GGAAGAGAGGTA-5'*
5'-CTCCAT(T)$_8$CCCTATAGTGAGTCGTATTAT
(Helper Oligonucleotide)

Anneal ↓

*GGAAGAGAGGTA-5'*
5'-CTCTGCACCCATCTCTCTCCTTCTCTCCAT(T)$_8$CCCTATAGTGAGTCGTATTAT

Ligate ↓

5'-CTCTGCACCCATCTCTCTCCTTCTCTCCAT(T)$_8$CCCTATAGTGAGTCGTATTAT
(Sequencing Length Oligonucleotide)

Anneal
Sequncing
Primer ↓

*GGATATCACTCAGCATAATA*-$^{32}$P
5'-CTCTGCACCCATCTCTCTCCTTCTCTCCAT(T)$_8$CCCTATAGTGAGTCGTATTAT

↓ Polymerase Extension
  Dideoxy Termination

Sequencing Gel (8% PAGE)

SEQUENCE LISTING ( 1 ) GENERAL INFORMATION:

( i i i ) NUMBER OF SEQUENCES: 5

( 2 ) INFORMATION FOR SEQ ID NO:1:

( i ) SEQUENCE CHARACTERISTICS:
      ( A ) LENGTH: 25 base pairs
      ( B ) TYPE: nucleic acid
      ( C ) STRANDEDNESS: single
      ( D ) TOPOLOGY: linear ( i i ) MOLECULE TYPE: DNA (genomic)

( i i i ) HYPOTHETICAL: NO ( x i ) SEQUENCE DESCRIPTION: SEQ ID NO:1:

CTCTCGCACC CATCTCTCTC CTTCT          2 5

( 2 ) INFORMATION FOR SEQ ID NO:2:

( i ) SEQUENCE CHARACTERISTICS:
      ( A ) LENGTH: 12 base pairs
      ( B ) TYPE: nucleic acid
      ( C ) STRANDEDNESS: single
      ( D ) TOPOLOGY: linear ( i i ) MOLECULE TYPE: DNA (genomic)

( i i i ) HYPOTHETICAL: NO ( i v ) ANTI-SENSE: YES ( x i ) SEQUENCE DESCRIPTION: SEQ ID NO:2:

ATGGAGAGAA GG          1 2

( 2 ) INFORMATION FOR SEQ ID NO:3:

( i ) SEQUENCE CHARACTERISTICS:
      ( A ) LENGTH: 35 base pairs
      ( B ) TYPE: nucleic acid
      ( C ) STRANDEDNESS: single
      ( D ) TOPOLOGY: linear ( i i ) MOLECULE TYPE: DNA (genomic)

( i i i ) HYPOTHETICAL: NO ( x i ) SEQUENCE DESCRIPTION: SEQ ID NO:3:

CTCCATTTTT TTTTCCCTAT AGTGAGTCGT ATTAT      3 5

( 2 ) INFORMATION FOR SEQ ID NO:4:

( i ) SEQUENCE CHARACTERISTICS:
      ( A ) LENGTH: 20 base pairs
      ( B ) TYPE: nucleic acid
      ( C ) STRANDEDNESS: single
      ( D ) TOPOLOGY: linear ( i i ) MOLECULE TYPE: DNA (genomic)

( i i i ) HYPOTHETICAL: NO ( i v ) ANTI-SENSE: YES ( x i ) SEQUENCE DESCRIPTION: SEQ ID NO:4:

```
         ATAATACGAC TCACTATAGG                                        20
```

( 2 ) INFORMATION FOR SEQ ID NO:5:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( x i ) SEQUENCE DESCRIPTION: SEQ ID NO:5:

```
         CAGAGCAAAA TCATCAGAAG A                                      21
```

METHOD FOR SEQUENCING SYNTHETIC OLIGONUCLEOTIDES CONTAINING NON-PHOSPHODIESTER INTERNUCLEOTIDE LINKAGES

BACKGROUND OF THE INVENTION

1. Field of the Invention

The invention relates to synthetic oligonucleotides, which are useful for a variety of purposes, including their use as antisense chemotherapeutic agents. More particularly, the invention relates to determining the nucleotide sequence of such oligonucleotides having non-phosphodiester internucleotide linkages at one or more positions within the oligonucleotide.

2. Summary of the Related Art

Synthetic oligonucleotides are useful for a wide variety of purposes. Of recent interest is the use of synthetic oligonucleotides to inhibit specific gene function. Oligonucleotides useful for this purpose are commonly complementary to a coding or "sense" strand of RNA and hence are known as antisense oligonucleotides. Antisense oligonucleotides that inhibit a variety of gene functions are now known in the art.

Zamecnik and Stephenson, Proc. Natl. Acad. Sci. USA 7.5:280–284 (1978), first showed oligonucleotide-mediated inhibition of virus replication in tissue culture, using Rous Sarcoma Virus.

Zamecnik et al., Proc. Natl. Acad. Sci. USA 83:4143–4146 (1986), demonstrated inhibition in tissue culture of the HTLV-III virus (now called HIV-1) associated with AIDS.

Of especial interest are synthetic antisense oligonucleotides having one or more internucleotide linkage that is a nonphosphodiester linkage. Such oligonucleotides are important to antisense chemotherapeutic approaches due to their relative resistance to nucleolytic degradation, compared with oligonucleotides having exclusively phosphodiester internucleotide linkages. Many such modified internucleotide linkages have been described in the art.

Agrawal et al., Proc. Natl. Acad. Sci. USA 85:7079–7083 (1988), teaches inhibition in tissue culture of HIV-1 with increased efficacy, using oligonucleotide phosphoramidates and phosphorothioates.

Sarin et al, Proc. Natl. Acad. Sci. USA 85:7448–7451 (1988), teaches inhibition in tissue culture of HIV-1 with increased efficacy, using oligonucleoside methylphosphonates.

Agrawal et al., Proc. Natl. Acad. Sci. USA 86:7790–7794 (1989), teaches nucleotide sequence specific inhibition of HIV-1 in both early-infected and chronically-infected cell cultures, using oligonucleotide phosphorothioates.

Leiter et al., Proc. Natl. Acad. Sci. USA 87:3430–3434 (1990), teaches inhibition in tissue culture of influenza virus replication by oligonucleotide phosphorothioates.

Unfortunately, oligonucleotides useful for the antisense chemotherapeutic approach are too short to be sequenced by conventional sequencing methodologies. Nevertheless, correct sequences are required for efficacy, and quality control procedures are needed to ensure that synthetic oligonucleotides have the desired nucleotide sequences. At present, the sequences of such oligonucleotides are often assumed to be correct based on the step-by-step synthesis itself since there is no convenient method available for their sequence analysis, particularly where oligonucleotides having non-phosphodiester internucleotide linkages are concerned.

Previous methods of analyzing oligonucleotides have been laborious for commercial applications. Agrawal et al., J. Chromatography 509:396–399 (1990) discloses analysis of oligonucleotide phosphorothioates involving conversion of phosphorothioate linkages to phosphodiesters followed by digestion with snake venom phosphodiesterase, phosphatase treatment and analysis of base composition on reversed phase HPLC.

There remains a need for simpler and more reliable determination of the nucleotide sequence of synthetic oligonucleotides, particularly for those oligonucleotides having non-phosphodiester internucleotide linkages.

BRIEF SUMMARY OF THE INVENTION

The invention provides, for the first time, an efficient and reliable method for determining the nucleotide sequence of synthetic oligonucleotides. In particular, the invention provides such a method for oligonucleotides having one or more non-phosphodiester internucleotide linkage at the 3' end of the oligonucleotide.

In the method according to the invention, four oligonucleotides are used. A first oligonucleotide is the sample oligonucleotide, which is the oligonucleotide to be sequenced. A second oligonucleotide is a "helper" oligonucleotide that is ligated to the 3' end of the sample oligonucleotide to provide an oligonucleotide of a sufficient length for the sequencing procedure (known as a "sequencing-length" oligonucleotide). A third oligonucleotide is a "molecular tack" oligonucleotide having a sequence that is complementary to both the 3' end of the sample oligonucleotide and the 5' end of the helper oligonucleotide.

These three oligonucleotides are annealed together, with the molecular tack oligonucleotide holding the 3' end of the sample oligonucleotide together with the 5' end of the helper oligonucleotide. The sample and helper oligonucleotides are then ligated together to form a sequencing-length oligonucleotide. A fourth oligonucleotide, which is a labelled primer oligonucleotide having a sequence complementary to a portion of the helper oligonucleotide is then annealed to the sequencing-length oligonucleotide and sequencing is carried out using, e.g., the Sanger dideoxy chain termination method or the Maxam and Gilbert chemical cleavage method of sequencing.

DETAILED DESCRIPTION OF THE INVENTION

Figure 1:
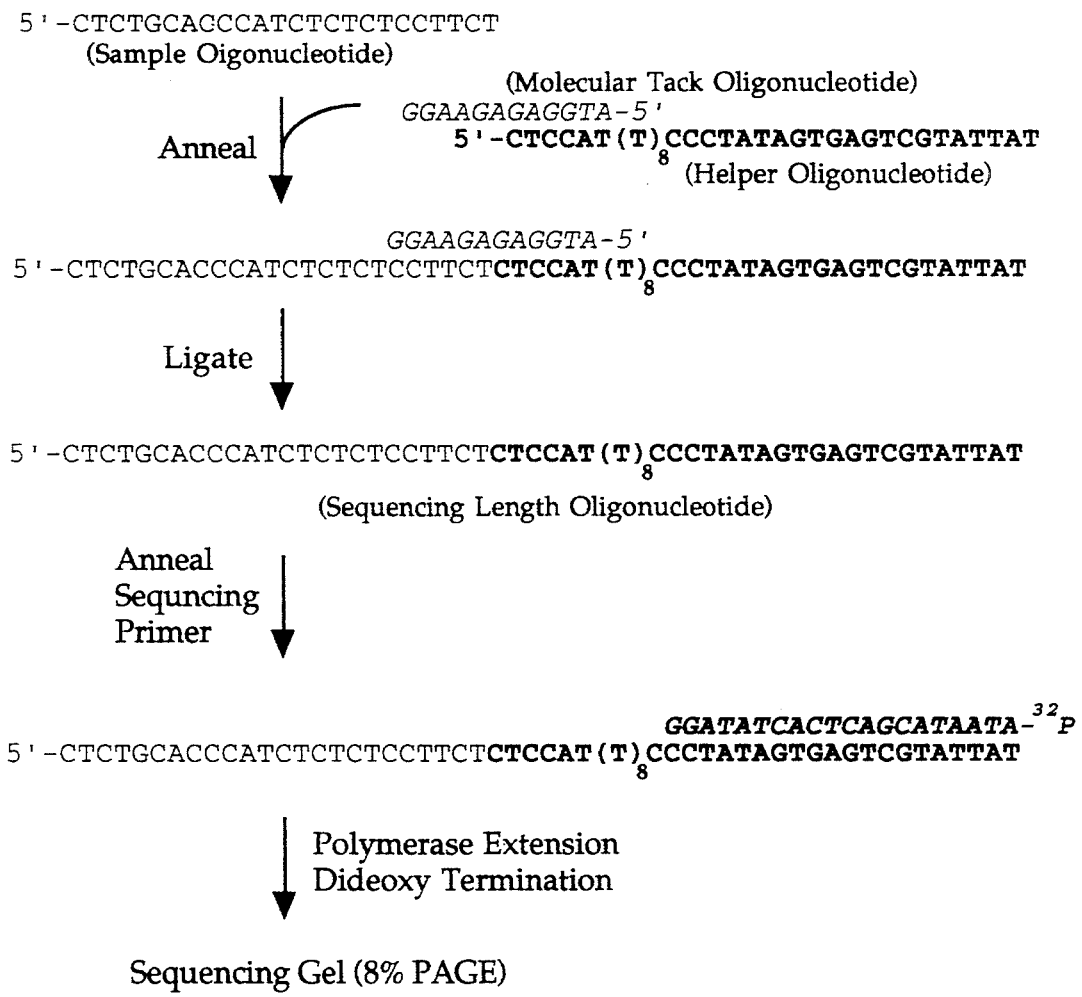
FIG. 1 summarizes the procedure according to the invention for sequencing synthetic oligonucleotides.

In a first aspect, the invention provides an efficient and reliable method for determining the nucleotide sequence of synthetic oligonucleotides. Generally, conventional methods for determining nucleotide sequences are difficult to use for synthetic oligonucleotides because such oligonucleotides are too short to serve as an efficient template. The method according to the invention overcomes this problem by providing a sequencing-length oligonucleotide that includes the sample oligonucleotide to be sequenced and that is long enough to serve as an efficient template.

In a second aspect, the invention provides an efficient and reliable method for determining the nucleotide sequence of synthetic oligonucleotides having one or more non-phosphodiester internucleotide linkage at the 3' end of the oligonucleotide. Oligonucleotides having phosphodiester linkages at the 3' end of the oligonucleotide can be extended by using terminal deoxynucleotide transferase to provide a molecule of suitable length for sequencing. However, terminal deoxynucleotide transferase is rather specific in its requirement for a phosphodiester internucleotide linkage at the 3' end of the oligonucleotide to be extended. Consequently, synthetic oligonucleotides having one or more non-phosphodiester nucleotide linkage at the 3' end tend to be poor substrates for terminal deoxynucleotide transferase. The method of the invention overcomes this problem by using a ligase enzyme to join the sample oligonucleotide to a helper oligonucleotide, thereby providing a sequencing-length oligonucleotide that is a suitable template for sequencing using conventional nucleic acid sequencing procedures, such as the Sanger dideoxy chain termination or Maxam and Gilbert chemical cleavage method. Ligases are less specific in their requirements for terminal internucleotide linkages than terminal deoxynucleotide transferase and thus can be used to join oligonucleotides having non-phosphodiester internucleotide linkages.

According to either aspect of the present invention, the method according to the invention comprises the following steps. First, three oligonucleotides are annealed together: a sample oligonucleotide, the nucleotide sequence of which is to be determined, a helper oligonucleotide to provide length, and a molecular tack oligonucleotide to hold the sample and helper oligonucleotides together. Second, the sample and helper oligonucleotides are ligated together to form a sequencing-length oligonucleotide. Any of the available, well known ligases can be used to effect this ligation. In a preferred embodiment, T4 DNA ligase is used. Third, a labelled primer oligonucleotide is annealed to the helper oligonucleotide portion of the sequencing-length oligonucleotide. Fourth, the primer is extended by a polymerase enzyme. Many polymerase enzymes are know in the art. All of these are suitable in principle. Preferably, a DNA polymerase will be used, most preferably Taq DNA polymerase. In this primer extension step dideoxynucleotides are included if the sequence determination is to be carried out according to the Sanger method. If the Maxam and Gilbert method of sequence determination is to be used, it is not necessary to use dideoxynucleotides. The Maxam and Gilbert method then requires an additional chemical cleavage step that is not used for the Sanger method. Both the Sanger and the Maxam and Gilbert methods are well known in the art and will not be described in further detail here. Finally, the dideoxy-terminated or chemically cleaved oligonucleotide sequences are fractionated according to standard procedures that separate molecules according to size (e.g., chromatography, electrophoresis). In a preferred embodiment, the molecules are separated electrophoretically on a sequencing gel. The fractionation pattern of the sequences is then interpreted by conventional procedures to determine the nucleotide sequence of the sample oligonucleotide.

In the method according to the invention, any sample oligonucleotide can, in principle, be sequenced. Preferably, sample oligonucleotides in the method according to the invention will range from about 4 to about 100 nucleotides in length. Most preferably, such sample oligonucleotides will range from about 8 to about 50 nucleotides. In principle, sample oligonucleotides can have any type of internucleotide linkages or even any combination of different types of internucleotide linkages, as long as the sample oligonucleotide can be ligated to the helper oligonucleotide and can be extended by the polymerase. For any given sample oligonucleotide, these parameters can be determined empirically, without undue experimentation, simply by carrying out test ligation and primer extension reactions using the conditions set forth in the experimental section of this specification. In a preferred embodiment, sample oligonucleotides will have at least one internucleotide linkage at the 3' end that is a non-phosphodiester linkage. Such sample oligonucleotides may have more than one non-phosphodiester linkage, up to having all non-phosphodiester linkages. The non-phosphodiester linkages present in the sample oligonucleotide preferably may include at least phosphorothioate, alkylphosphonate, phosphoramidate, alkylphosphonothioate, phosphodithioate, and sulfone, sulfate, keto, phosphate ester, bridged phosphorothioate and bridged phosphoramidate linkages, all of which are known in the art. Sample oligonucleotides having phosphorothioate internucleotide linkages are most preferred.

In the method according to the invention a helper oligonucleotide is ligated to the sample oligonucleotide via a phosphate at the 5' end of the helper oligonucleotide or the 3' end of the sample oligonucleotide to provide a sequencing-length oligonucleotide having sufficient length to serve as a template for sequencing reactions. The helper oligonucleotides may vary in length depending on the length of the sample oligonucleotide, since the important parameter is the length of the overall sequencing-length oligonucleotide. Thus, for longer sample oligonucleotides shorter helper oligonucleotides may be used, whereas for shorter sample oligonucleotides longer helper oligonucleotides will be required. Preferably, the sequencing-length oligonucleotide will range from about 8 to about 50 nucleotides in length. The helper oligonucleotide will thus be varied in length to provide a sequencing-length oligonucleotide in the appropriate size range for any given sample oligonucleotide. The helper oligonucleotide can have any nucleotide sequence and can have any type of internucleotide linkages or mixture of different internucleotide linkages, as long as it can be ligated to the sample oligonucleotide and can serve as a template for extension of the primer oligonucleotide by polymerase. These parameters can be readily determined without undue experimentation for any given helper oligonucleotide by simply carrying out test ligations and primer extensions under the conditions set forth in the experimental sections of this specification. In one preferred embodiment, the helper oligonucleotide will be an oligonucleotide phosphodiester.

In the method according to the invention, the sample and helper oligonucleotides are held together for ligation by a third oligonucleotide, which is denoted a "molecular tack" oligonucleotide. The molecular tack oligonucleotide holds the sample and helper oligonucleotides together by annealing to the 3' end of the sample oligonucleotide and the 5' end of the helper oligonucleotide. Thus, the molecular tack oligonucleotide must have a nucleotide sequence comprising a 5' region that is complementary to the 5' end of the helper oligonucleotide and an adjacent 3' region that is complementary to the 3' end of the sample oligonucleotide. The molecular tack oligonucleotide may be of any length as long as its regions that are complementary to the helper and sample oligonucleotides are of sufficient length to anneal to both the helper and sample oligonucleotides. Preferably, the molecular tack oligonucleotide will range from about 8 to about 50 nucleotides in length and will have a 5' region with a least 4 nucleotides complementary to the 5' end of the helper oligonucleotide adjacent to a 3' region with at least 4 nucleotide complementary to the 3' end of the sample oligonucleotides. Most preferably, the molecular tack will be from about 8 to about 20 nucleotides in length.

The fourth oligonucleotide used in the method according to the invention is a primer oligonucleotide for polymerase extension. This primer oligonucleotide can be any of the conventional types of oligonucleotides that are well known and commonly used for DNA sequencing or primer extension reactions. The primer oligonucleotide will have a sequence that is complementary to all or a portion of the helper oligonucleotide. Preferably, the 3' end of the primer oligonucleotide will be complementary to a portion of the helper oligonucleotide that is from about 10 to about 15 nucleotides from the 3' end of the sample oligonucleotide portion of the sequencing-length oligonucleotide.

The following examples are intended to further illustrate certain preferred embodiments of the method according to the invention and are not intended to be limiting in nature. Except where otherwise indicated, the materials and conditions used in the following examples are as follows.

[γ-$^{32}$P] ATP (3000 Ci/mmol) was obtained from NEN DuPont. T4-polynucleotide kinase, T4-DNA ligase, Taq-DNA polymerase and dideoxynucleosides triphosphate were obtained from Promega. Oligodeoxynucleotides and oligonucleotide phosphorothioates were prepared by using DNA synthesizer (Millipore, Model 8700) with phosphoramidite chemistry. Deprotection of oligonucleotides was carried out with conc. NH$_4$OH at 55° C. for 8 hours. Purification was carried out using 20% polyacrylamide (7M urea) gel electrophoresis.

EXAMPLE 1

Ligation of Sample and Helper Oligomers

Kination of "helper oligomer" (5'-CTCCATTTTTTTTTCCCTATAGT GAGTCGTATTAT, 35-mer) (SEQ ID No: 3) was done by T4-polynucleotide kinase by using the conditions described in Example 2 except using only cold ATP. A third oligomer, a 12-mer "molecular tack oligomer" was synthesized in which the 5'-half sequence was ATGGAG and the 3'-half sequence was complementary with 3'-end of the sample. 100 pmole of 5'-kinated "helper oligomer" was mixed with 200 pmole of the sample and "molecular tack oligomer" in a mixture (final volume 18 μl) containing 2 μl of 10×ligase buffer (300 mM Tris., pH 7.8, 100 mM MgCl$_2$, 100 mM DTT and 10 mM ATP). The reaction mixture was incubated at 37° C. for 15 minutes and then cooled down in an ice bath. 2 μl T4-DNA ligase (3000 units/ml) was added to the mixture and kept at 4° C. overnight followed by inactivation of the ligase at 70° C. for 5 minutes. Over 90% ligation was obtained. The mixture was then used as template of sequencing without further purification.

EXAMPLE 2

Labelling 5'-ends Of Sequencing Primer 200 pmole of T7 primer (5'-TAATACGACTCACTATAGG) (SEQ ID No: 4) was mixed with 300 pmole of [γ-$^{32}$P] ATP (20 μCi) and 15 units of T4-polynucleotide kinase in a reaction mixture (final volume 15 μl) of 50 mM Tris., pH 7.5, 10 mM MgCl$_2$ and 5 mM DTT. The reaction mixture was incubated at 37° C. for 40 minutes, followed by inactivation of the kinase at 70° C. for 5 minutes. 5'-end labelled primer was purified by 20% denaturing polyacrylamide gel electrophoresis, then the primer band was cut out and eluted with 0.5M ammonium acetate overnight at room temperature and precipitated by ethanol (4 volumes).

EXAMPLE 3

Carrying Out The Sequencing Reaction 5 pmole of the template from the ligation mixture was mixed with 15 pmole of 5'-end $^{32}$P-labelled primer in a mixture (final volume 25 μl) of 50 mM Tris., pH 9.0, and 10 mM MgCl$_2$. The mixture was incubated at 37° C. for 10 minutes, followed by addition of 1.5 μl Taq DNA polymerase (2500 units/ml) and division into 4 tubes (6 μl each), which were labelled G, A, T and C. To the corresponding tube, 1 μl of the appropriate d/ddNTP mix (see Table I) was added and the reaction mixture was incubated at 70° C. for 15 minutes, then 1 μl of chase mixture (dGTP, dATP, dCTP, dTTP 25 mM each) was added to each tube, which was then incubated at 70° C. for another 15 minutes. To stop the reaction 4 μl of stop solution (10 mM NaOH, 85% formamide, 0.05% bromophenol blue and 0.05% Xylene Cyanol) was added, followed by heating at 70° C. for 5 minutes before loading onto the sequencing gel.

TABLE I

| Formulations Of d/ddNTPs Use For Sequencing | | | | |
|---|---|---|---|---|
| Component | G Mix | A Mix | T Mix | C Mix |
| ddGTP | 110 μM | — | — | — |
| ddATP | — | 1230 μM | — | — |
| ddTTP | — | — | 1600 μM | — |
| ddCTP | — | — | — | 890 μM |
| dGTP | 25 μM | 230 μM | 230 μM | 230 μM |
| dATP | 250 μM | 23 μM | 23 μM | 230 μM |
| dTTP | 250 μM | 230 μM | 23 μM | 230 μM |
| dCTP | 250 μM | 230 μM | 230 μM | 230 μM |

EXAMPLE 4

Sequencing Gel Electrophoresis

An 8% polyacrylamide gel (7M urea, 50 mM Tris-borate, pH 8.3 and 2.5 MM EDTA) 40 cm long, 30 cm wide and 0.75 mm thick was loaded with the product of Example 3. The running buffer was 50 mM tris-borate, pH 8.3 containing 2.5 mM EDTA. The samples were loaded onto the gel and electrophoresed at 600 V, 50 mA until the bromophenol blue dye marker was about 5 cm from the bottom of the gel. The gel was dried and autoradiographed.

Figure 2:
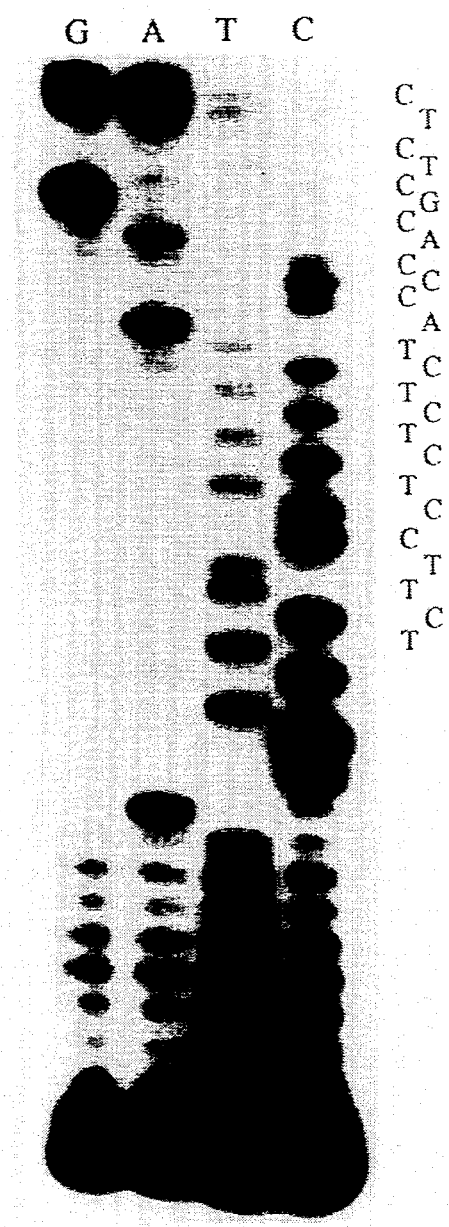
FIG. 2 shows the result of sequencing according to the method of the invention for an oligonucleotide phosphorothioate having the nucleotide sequence 5'-CTCTCGCACCCATCTCTCTCCTTCT -3' (SEQ ID NO: 1).
Figure 3:
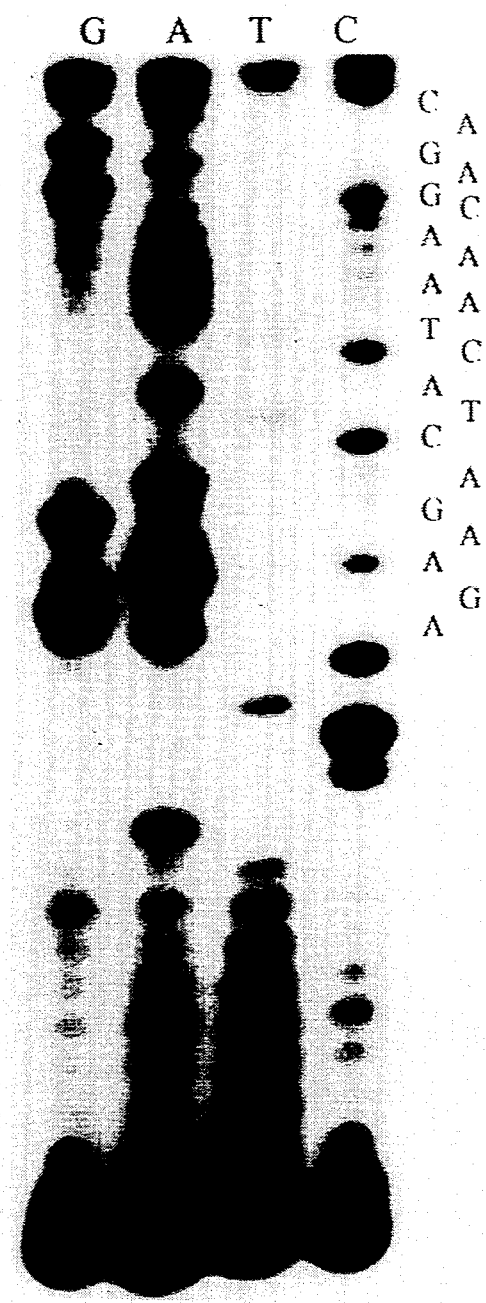
FIG. 3 shows the result of sequencing according to the method of the invention for an oligonucleotide phosphorothioate having the nucleotide sequence 5'-CAGAGCAAAATCATCAGAAGA -3' (SEQ ID NO: 5).

The results are shown for two different oligonucleotide phosphorothioates in FIGS. 2 and 3. These results demonstrate that the method of the invention works well with oligonucleotides having non-phosphate internucleotide linkages, in this case phosphorothioate linkages. The method was successful for both of these divergent sequences, indicating that its success is independent of the base composition of the sample oligonucleotide. The only limitation to the method appears to be that the 5'-end single nucleotide could not be determined. Thus, the nature of this nucleotide will have to be verified by methods for terminal analysis.

We claim:

1. A method for determining the nucleotide sequence of a single-stranded sample oligonucleotide except for its 5'-terminal nucleotide, comprising the steps of:
   (a) annealing the sample oligonucleotide and a single-stranded helper oligonucleotide, each having 5' and 3' ends, with a single-stranded molecular tack oligonucleotide having a 5' region complementary to the 5' end of the helper oligonucleotide and an immediately adjacent 3' region complementary to the 3' end of the sample oligonucleotide, the sequence of at least three of the 3'-terminal nucleotides of the sample oligonucleotide being known;
   (b) ligating the helper oligonucleotide to the sample oligonucleotide to yield a sequencing-length oligonucleotide;
   (c) annealing a labelled primer oligonucleotide to the helper oligonucleotide portion of the sequencing-length oligonucleotide, the primer oligonucleotide having a nucleotide sequence that is complementary to a portion of the helper oligonucleotide;
   (d) extending the primer oligonucleotide with a polymerase in the presence of chain-extending and chain terminating nucleoside triphosphates;
   (e) fractionating the extended primers according to standard procedures; and
   (f) determining the nucleotide sequence of the sample oligonucleotide, except for its 5'-terminal nucleotide, from the fractionated extended primers.

2. The method according to claim 1, wherein the sample oligonucleotide has one or more non-phosphodiester internucleotide linkage at a 3' end.

3. The method according to claim 2, wherein the non-phosphodiester internucleotide linkage is a phosphorothioate linkage.

4. A method for determining the nucleotide sequence of a single-stranded sample oligonucleotide except for its 5'-terminal nucleotide comprising the steps of:
   (a) annealing the sample oligonucleotide and a single-stranded helper oligonucleotide, each having 5' and 3' ends, with a single-stranded molecular tack oligonucleotide having a 5' region complementary to the 5' end of the helper oligonucleotide and an immediately adjacent 3' region complementary to the 3' end of the sample oligonucleotide, the sequencing at least three of the 3'-terminal nucleotides of the sample oligonucleotide being known;
   (b) ligating the helper oligonucleotide to the sample oligonucleotide to yield a sequencing-length oligonucleotide;
   (c) annealing a labelled primer oligonucleotide to the helper oligonucleotide portion of the sequencing-length oligonucleotide, the primer oligonucleotide having a nucleotide sequence that is complementary to a portion of the helper oligonucleotide;
   (d) extending the primer oligonucleotide with a polymerase to yield a primer extension product;
   (e) cleaving the primer extension product with appropriate Maxam and Gilbert sequencing reagents to yield cleaved primer extension products;
   (f) fractionating the cleaved primer extension products according to standard procedures; and
   (g) determining the nucleotide sequence of the sample oligonucleotide except for its 5'-terminal nucleotide, from the fractionated cleaved primer extension products.

5. The method according to claim 4, wherein the sample oligonucleotide has one or more non-phosphodiester internucleotide linkage at a 3' end.

6. The method according to claim 5, wherein the non-phosphodiester internucleotide linkage is a phosphorothioate linkage.

* * * * *